United States Patent [19]

Chul

[11] Patent Number: 5,492,127
[45] Date of Patent: Feb. 20, 1996

[54] METHOD OF USING A DIAGNOSTIC APPARATUS FOR FUNCTIONAL EXAMINATION OF A HUMAN CIRCULATORY ORGAN SYSTEM

[75] Inventor: Baek K. Chul, Seoul, Rep. of Korea

[73] Assignee: Sony Corporation, Tokyo, Japan

[21] Appl. No.: 276,756

[22] Filed: Jul. 18, 1994

Related U.S. Application Data

[63] Continuation of Ser. No. 789,424, Nov. 4, 1991, abandoned, which is a continuation-in-part of Ser. No. 657,603, Feb. 15, 1991, abandoned, which is a continuation of Ser. No. 533,285, Jun. 5, 1990, abandoned.

[30] Foreign Application Priority Data

Aug. 31, 1989 [JP] Japan ................................ 1-223347

[51] Int. Cl.$^6$ ........................................... A61B 5/0255
[52] U.S. Cl. ........................................................ 128/687
[58] Field of Search .................................. 128/687, 691, 128/715

[56] References Cited

U.S. PATENT DOCUMENTS

| | | | |
|---|---|---|---|
| 4,066,066 | 1/1978 | Paek | 128/688 |
| 4,195,642 | 4/1980 | Price et al. | 128/689 |
| 4,362,164 | 12/1982 | Little et al. | 128/715 |
| 4,572,199 | 2/1986 | La Course | 128/688 |

Primary Examiner—William E. Kamm
Attorney, Agent, or Firm—Abelman, Frayne & Schwab

[57] ABSTRACT

A diagnostic apparatus for a functional examination of a circulatory organ system, comprising a sensor portion of a microphone which is provided on three points of the pulsing points near the wrist consisting of Point 1 (sun), Point 2 (seki), Point 3 (shaku), a signal process portion, a filter portion and a display portion, and then the wavy patterns detected by said sensor portion are visibly displayed by being filtered at said filter portion.

3 Claims, 4 Drawing Sheets

METHOD OF USING A DIAGNOSTIC APPARATUS FOR FUNCTIONAL EXAMINATION OF A HUMAN CIRCULATORY ORGAN SYSTEM

BACKGROUND OF THE INVENTION

FIELD OF THE INVENTION

The present application is a continuation of Ser. No. 07/789,424, filed Nov. 4, 1991, which is a continuation-in-part application of Ser. No. 07/657,603, filed on Feb. 15, 1991, which is a Rule 62 continuation of Ser. No. 07/533,285, filed Jun. 5, 1990, all of which are now abandoned.

The present invention relates to a method and apparatus for assisting a medical practitioner in sensing and categorizing various vascular pulses found at different locations in the human body. Multiple microphones are used to duplicate the kinetic sensations which have in the past been sensed by the human fingers. More specifically, each microphone is located on the human body undergoing diagnosis along the radial artery at point corresponding to the sun, seki, and shaku locations which have been described in old Chinese medical books. The present invention provides a diagnostic apparatus for a functional examination of the circulatory organ system, and more particularly to a useful technique applicable to a pulse diagnostic apparatus for Chinese medicine, an electrocardiograph and the like.

DESCRIPTION OF THE PRIOR ART

As a diagnostic apparatus for executing a functional examination of circulatory organs of human body, a sphygmomanometer, an electrocardiograph, a plethysmography apparatus and the like are provided in Occidental medicine, and a pulse diagnostic record apparatus such as U.S. Pat. No. 4,06,006 is familiar in Chinese medicine.

The above apparatus have a point of sameness in that physiological variation of circulatory organs is visibly expressed by using electronic devices. Namely, an electrocardiograph, a plethysmography apparatus, a pulse diagnostic record apparatus and the like record natural signals occurring in the human body, specifically occurring in a circulatory organ system, through a series of amplifying circuits. The shapes of so-recorded graphs are analyzed and such graphs are used as materials for evaluating the state of the human body.

The above-mentioned electrocardiograph records the potential difference generated by the pulse of heart and judges the function of heart. It secures a large number of readings. However, the electrocardiogram has drawbacks. When it is used in a clinical examination, in considerable cases, the judgement of heart disease is not made by the results obtained from the electrocardiogram, but from the reading of electrocardiogram together with clinical observations.

On the other hand, a plethysmography is a newer technology. It records a plethysmogram on torraditional factors, velocity and acceleration, together with an amount of blood flow moving along with capillaries, in order to exceed the quality of diagnoses which can be made with an electrocardiogram. With a plethysmography, it is possible to diagnose several diseases, especially the diseases of adult people (see U.S. Pat. Nos. 3,881,481; 3,920,004; 4,154,238 and 4,432,374).

Moreover, a pulse diagnostic record apparatus of the above mentioned U.S. Pat. No. 4,066,066, records in each portion of pulse diagnosis the wavy pattern of vibration which is obtained in a circuit utilized for an existing plethysmogram by piezoelectric effects based on a sensing method. The diagnosis of various diseases is made possible by analyzing the so-obtained record, in a manner corresponding to the eastern medicine system.

As described above, the plethysmogram and the pulse diagnostic record are similar in that they facilitate diagnoses of diseases in the circulatory system. However, they are analyzing materials for examining the circulatory system as compared with several predetermined basic wavy patterns. When done in the form of graph, such examination is relatively simple.

Namely, since the wavy patterns to be obtained by the above-mentioned pulse diagnostic record apparatus and the existing electrocardiograph are complex in form, the operators have to gain experience to give the appropriate judgement by observing numerous graphs. Additionally, the operators are forced to give the subjective judgement. As the result, the apparatus of the prior art is not sufficiently satisfactory for the wide usability.

SUMMARY OF THE INVENTION

Taking into consideration the above-mentioned prior art, an object of the present invention is to provide a method of using such a diagnostic apparatus for a functional examination of a circulatory organ system that displays specifically and visibly the characteristic of examining diseases.

In order to achieve the above-mentioned object, the apparatus of the present invention is characterized in that it comprises: a sensor means having a plurality of microphones, one microphone is respectively provided on each of three (3) points of the pulsing points near the wrist consisting of Point 1 (sun), Point 2 (seki or kan), and Point 3 (shaku) which are stylus portions of an antebrachial bone of an arm, microphones detect the pulses of the points, which are generated by pulsation of the heart; a signal process means having a plurality of signal process means, each signal process means amplifying output signals from its respective microphone of the sensor means; a filter means having a plurality of filter means, each filter means filters out the components outside a specific frequency band, of which the peak frequency is in the vicinity of 20 Hz, of the output signals from the signal process means and a display means having at least one display device, which displays the filtered output signals from the filter means as a visible graph.

According to the present invention of the above-mentioned construction, the wavy patterns of pulses detected by the sensor means are filtered by the filter means passing the specific frequency band, 14 Hz to 37 Hz, of which the peak frequency is in the vicinity of 20 Hz. As a result, the so-called wavy patterns become ones in which the characteristics necessary for the examination are emphasized.

DETAILED DESCRIPTION OF THE PREFERRED EMBODIMENTS

Hereinafter, a preferred embodiment of the present invention will be explained by using the accompanying drawings.

Figure 1:
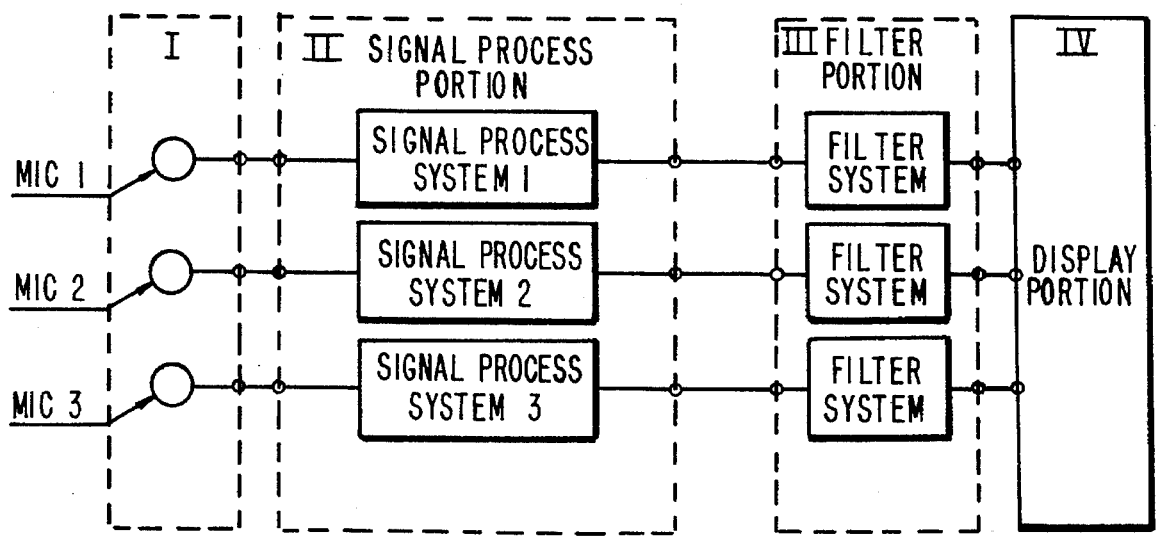
FIG. 1 is a block diagram showing an embodiment of the present invention, respectively.

In FIG. 1 showing the embodiment of the present invention, a sensor I is connected to a means IV for displaying results, through a means II for processing signals received from sensor I and a means III for filtering out unwanted signals. The sensor I is formed by crystal microphones Mic. 1, Mic. 2 and Mic. 3, each composed of piezoelectric elements, one of which is releasably provided on each point of Point 1 (sun), Point 2 (seki or kan) and Point 3 (shaku) of the pulsing points for detecting signals. Signal process means II amplifies output signals of the microphones Mic. 1 to Mic. 3 and in addition executes noise reduction. Filter means III filters frequency components outside of a specific frequency band of the output signal of the signal process means II and each output signal filtered by the filter means III is visible on a display means IV.

Figure 2:
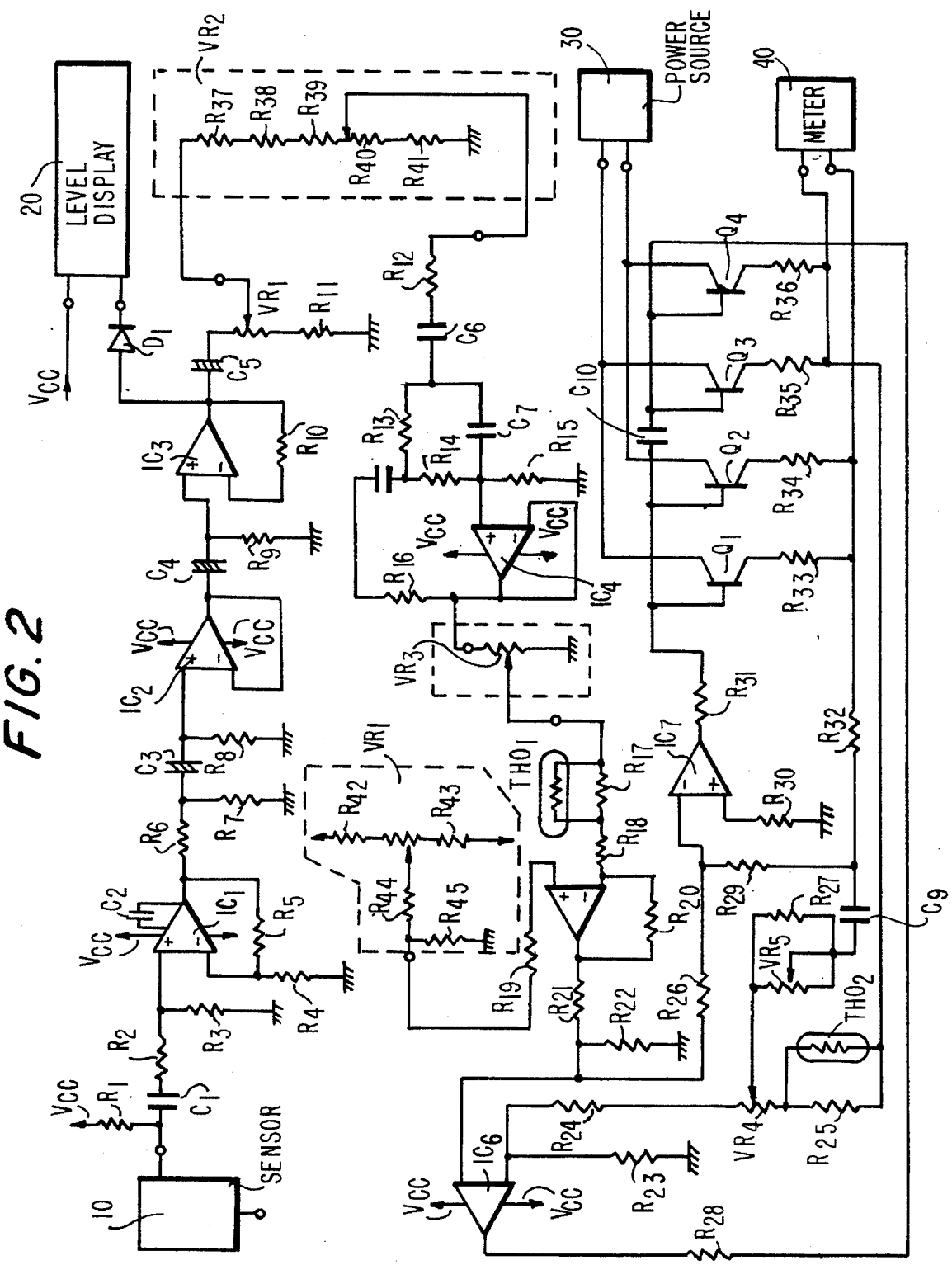
FIG. 2 is a detailed circuit diagram.

FIG. 2 is a circuit diagram showing a detailed composition of the above-mentioned embodiment. The figure shows one individual signal process means of the signal process means II. However, a pulse diagnostic apparatus in the embodiment has three signal process means connected in parallel, one of which is the same one as that shown in FIG. 2 and each signal process means processes one of the pulse waves of either Point 1 (sun), Point 2 (seki or kan), and Point 3 (shaku). As shown in FIG. 2, the output from one microphone of a sensor 10, which is formed of three crystal microphones, is input from the microphone into an OP amplifier IC1, through capacitor C1, and a resistance R2. The signal amplified by the OP amplifier IC1 has excess noise removed by resistances R6, R7, R8 and a capacitor C3, and the signal is input into OP amplifier IC2. The signal amplified by the OP amplifier IC2 is input into an OP amplifier IC3 through a capacitor C4 and a resistance R9. The signal amplified by the OP amplifier IC3 is input into a level display 20, amplitude of the signal is visibly display by the level 20, and additionally the signal is input into a variable resistance VR1, grounded by a resistance R11 through a capacitor C5. A slider of the variable resistance is connected to an external variable resistance VR2, whose one end is grounded. On the other hand, a slider of the external variable resistance VR2 is input into an OP amplifier IC4 through a resistance R12, capacitors C6, C7 and resistances R13 and R14. The output of the OP amplifier IC4 is input into OP amplifier IC5 through a variable resistance VR3 and resistances R17 and R18. In this portion, a temperature compensation thyristor TH01 is connected in parallel to the resistance R17.

The signal amplified by the OP amplifier IC5 is supplied to OP amplifiers IC6 and IC7 through a resistance R21. The output sides of the OP amplifiers IC6 and IC7 are connected to each other through a capacitor C10 and it is respectively connected to the bases of transistors Q1, Q2, Q3, and Q4. A power source 30 supplies the electric power to the transistors Q1 to Q4. A power amplifier of push-pull style comprises OP amplifiers IC6, IC7 and transistors Q1 to Q4. Since a galvanometer is used as a meter 40 in the embodiment, the above-mentioned power amplifier is provided to drive the meter 40. If an oscilloscope is used as the display means IV, the above mentioned power amplifier is unnecessary.

Figure 3:
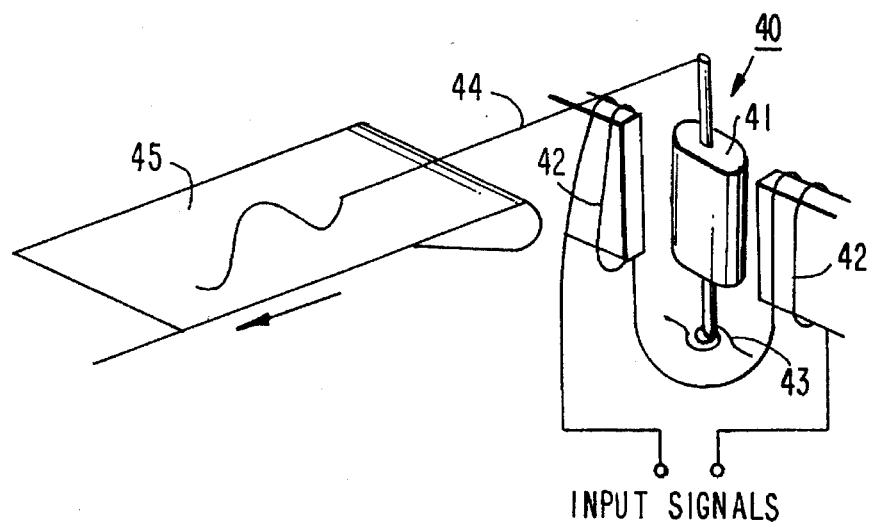
FIG. 3 is an explanatory picture showing conceptually the extracted meter.

The display means IV, formed of at least one display device, is provided in order to display a wavy pattern of each processed signal. The wavy patterns may be displayed on one display device or a plurality of the display devices. The display devices mechanically or electronically display the wavy pattern. For example, the meter 40 is a galvanometer. It and one of the filter means of the filter means III and one of the display devices of display means IV are united. The meter 40, shown in FIG. 3, comprises a magnet 41 of movable portion, a magnet coil 42 of fixed portion which interposes the magnet 41 and which is symmetrically disposed, a spring 43, a pen 44, and a graph paper 45. An amount of rotary movement of the magnet 41 alters correspondingly with the amplitude of output signal from the power amplifier which is supplied to the magnet coil 42, and the rotary movement is visibly displayed by drawing the amplitude corresponding to the rotary movement on the graph paper 45 with pen 44.

The amount of rotary movement of magnet 41 becomes zero when an electromagnetic force between the magnet 41 and the magnet coil 42, and a biasing force of the spring 43 are balanced. A resonance frequency of a mechanical vibration system of the meter 40 is altered by adjusting a spring constant of the spring 43. Accordingly, a desired frequency characteristic is set by adjusting a spring constant of spring 43.

Figure 4:
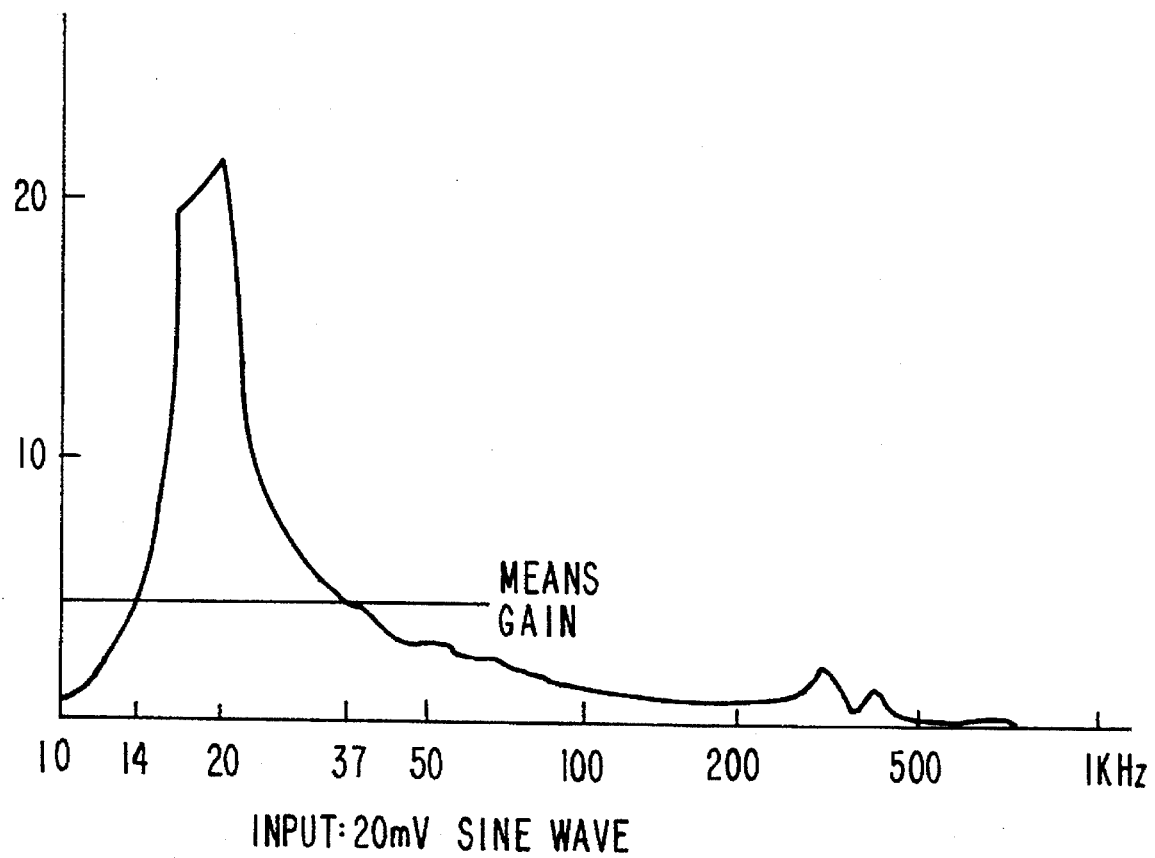
FIG. 4 shows the frequency characteristics of the filter system.

A frequency characteristic of the meter 40 in the case of this embodiment is shown in FIG. 4. As shown in FIG. 4, the meter 40 is used as a bandpass filter of which the peak frequency is the vicinity of 20 Hz.

Figure 5A:
FIG. 5(a) is a wavy pattern graph showing a wavy pattern before it is filtered.
Figure 5B:
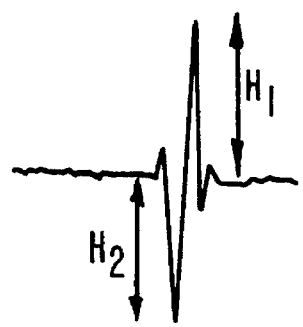
FIG. 5(b) is a wavy pattern graph showing a wavy pattern after it is filtered.
Figure 6A:
FIG. 6(a) is a wavy pattern graph showing a wavy pattern before it is filtered.
Figure 6B:
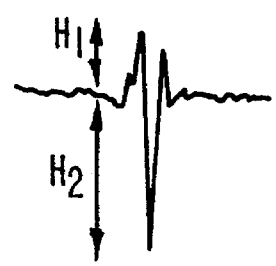
FIG. 6(b) is a wavy pattern graph showing a wavy pattern after it is filtered.
Figure 7A:
FIG. 7(a) is a wavy pattern graph showing a wavy pattern before it is filtered.
Figure 7B:
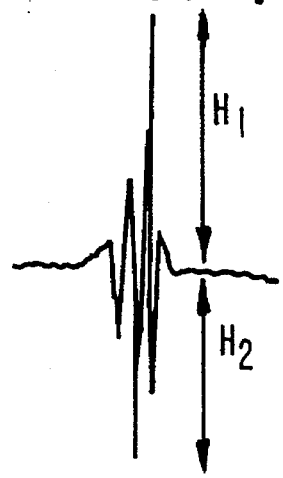
FIG. 7(b) is a wavy pattern graph showing a wavy pattern after it is filtered.

In the embodiment, the signals indicating a normal pulse, which are the output signals of the signal process means II, as shown in FIG. 5(a), are visibly displayed as a wavy pattern, as shown in FIG. 5(b), on the graph paper 45 of the display means IV. Hereinafter, as described above, a negative pulse shown in FIG. 6(a) is visibly displayed as a wavy pattern as shown in FIG. 6(b) and a positive pulse shown in FIG. 7(a) is visibly displayed as a wavy pattern as shown in FIG. 7(b). If referring to FIG. 5(b), 6(b), and 7(b), since the wavy patterns are more emphasized in their distinctive parts than those shown in FIG. 5(a), 6(a), and 7(a), they are recognized to be easier to read. If a range of the frequency band filtered by bandpass filter is outside the range of 14 Hz to 37 Hz, it cannot be visibly displayed clearly as a wavy pattern having a positive peak pulse point and a negative peak pulse point.

A condition of the human body is examined by calculating an equation $|H1-H2|$, wherein H1 is a height of the positive peak pulse point in a wavy pattern after filtering and H2 is a height of a negative peak pulse point in a wavy pattern after filtering. H1 and H2 are variables determined by each individual human body. If a result of the equation is zero, it means that the human body is normal. Unless the result of the equation is zero, it means that a detected human body is not in a normal condition and may require further attention.

Moreover, in the above-mentioned embodiment, the filter means III is formed by the mechanical vibration system of the meter 40. However, an electric filter having the same frequency band characteristic may be used, too. In the case of the electric filter, an oscilloscope is suitable for the display means IV at which each output signal of the OP amplifier IC5 in a respective circuit, as shown in FIG. 2, is input into and which each output signal of such filter is changed into the visible waves. Moreover, the present invention is applicable not only to a pulse diagnostic apparatus, but also to devices which perform a functional examination of a circulatory organ system, for example, an electrocardiograph.

As described above, since the wavy patterns detected by a sensor means are visibly displayed by using the filter means according to the present invention, a specific examination may be performed easily and objectively by observing the visible wavy patterns.

What is claimed is:

1. A method for functional examination of a human body's circulatory system comprising:

A. providing a diagnostic system for functional examination of a circulatory system which is comprised of at least a sensor means having three microphones for sensing the pulse present at three different body points, a band pass filter means for receiving the pulse signals from the microphones and filtering out the components which are outside of a predetermined frequency band ranging from 14 Hz to 37 Hz and having a peak frequency in the order of 20 Hz for producing filtered output signals, and a display means connected to the filter means for receiving the filtered output signals, and displaying the filtered output signals as visible graphs;

B. placing each of the microphones of the sensor means on a different one of three wrist points to detect the pulses at the points, each microphone placed to detect vibrations of the human body which are generated by a pulsation of the heart, the points consisting of Point 1 (sun), Point 2 (seki or kan), Point 3 (shaku), which are portions of an antebrachial bone of an arm;

C. presenting the microphone output signals to the band pass filter means to filter out components outside of a frequency band ranging from 14 Hz to 37 Hz, of which the peak frequency is in the order of 20 Hz to modify the wave form presentation of the microphone output signals;

D. presenting the output signals of the band pass filter means to the display means to display the modified wave form from each filtered output signal, which exhibits a positive pulse peak point H1 and a negative pulse peak point H2 which are clearly distinguishable in the visible graph and E. comparing the peak amplitudes of H1 and H2 to provide an indication of the condition of the circulatory system.

2. The method of claim 1 including the further step of measuring the heights $H_1$ and $H_2$ of the positive and negative pulse points of the modified wave forms, and determining their difference as an indication of the human body condition.

3. The method of claim 1 which includes the intermediate steps of presenting the pulse signals from the signal means to a signal processing means for amplifying and reducing the noise in the pulse signals before presenting the pulse signals to the band pass filter means.

* * * * *